US008383678B2

(12) United States Patent
Sachetto et al.

(10) Patent No.: US 8,383,678 B2
(45) Date of Patent: *Feb. 26, 2013

(54) TYPE A GELATIN CAPSULE CONTAINING PUFA IN FREE ACID FORM

(75) Inventors: Jean-Pierre Sachetto, Arlesheim (CH); Roly Bufton, Bubendorf (CH); Thomas Buser, Nuglar (CH)

(73) Assignee: Chrysalis Pharma AG, Sachseln (CH)

( * ) Notice: Subject to any disclaimer, the term of this patent is extended or adjusted under 35 U.S.C. 154(b) by 68 days.

This patent is subject to a terminal disclaimer.

(21) Appl. No.: 12/984,994

(22) Filed: Jan. 5, 2011

(65) Prior Publication Data

US 2011/0097394 A1 Apr. 28, 2011

Related U.S. Application Data

(63) Continuation of application No. 10/587,201, filed as application No. PCT/GB2005/000415 on Feb. 7, 2005, now Pat. No. 7,960,370.

(30) Foreign Application Priority Data

Feb. 13, 2004 (GB) ..................... 0403247

(51) Int. Cl.
*A61K 31/202* (2006.01)
*A61K 9/48* (2006.01)
(52) U.S. Cl. ..................... 514/549; 514/560
(58) Field of Classification Search ................. 514/549, 514/560
See application file for complete search history.

(56) References Cited

U.S. PATENT DOCUMENTS

| | | | |
|---|---|---|---|
| 2,870,062 | A | 1/1959 | Stanley et al. |
| 2,888,661 | A | 1/1959 | Tschentke et al. |
| 4,737,357 | A | 4/1988 | Lehmann et al. |
| 4,895,725 | A | 1/1990 | Kantor et al. |
| 4,910,021 | A | 3/1990 | Davis et al. |
| 4,917,900 | A | 4/1990 | Jones et al. |
| 4,935,243 | A | 6/1990 | Borkan et al. |
| 5,043,328 | A | 8/1991 | Weithmann |
| 5,252,333 | A | 10/1993 | Horrobin |
| 5,292,522 | A | 3/1994 | Petereit et al. |
| 5,401,512 | A | 3/1995 | Rhodes et al. |
| 5,411,988 | A | 5/1995 | Bockow et al. |
| 5,422,115 | A | 6/1995 | Horrobin |
| 5,502,077 | A | 3/1996 | Breivik et al. |
| 5,603,953 | A | 2/1997 | Herbig et al. |
| 5,792,795 | A | 8/1998 | Buser et al. |
| 5,834,512 | A | 11/1998 | Akimoto et al. |
| 5,843,482 | A | 12/1998 | Rhodes et al. |
| 5,874,470 | A | 2/1999 | Nehne et al. |
| 5,948,818 | A | 9/1999 | Buser et al. |
| 6,234,464 | B1 | 5/2001 | Krumbholz et al. |
| 6,555,316 | B1 | 4/2003 | Cohen et al. |
| 7,960,370 | B2 * | 6/2011 | Sachetto et al. ............... 514/183 |
| 2003/0064074 | A1 | 4/2003 | Chang et al. |
| 2003/0161872 | A1 | 8/2003 | Chen et al. |
| 2005/0089571 | A1 | 4/2005 | Beckert et al. |

FOREIGN PATENT DOCUMENTS

| | | |
|---|---|---|
| CA | 1151068 | 8/1983 |
| CA | 2522462 | 10/2004 |
| DE | 44 22 938 | 1/1995 |
| EP | 0 100 052 A1 | 2/1984 |
| EP | 0212746 | 3/1987 |
| EP | 0 225 189 A2 | 6/1987 |
| EP | 0225303 | 6/1987 |
| EP | 0244832 | 11/1987 |
| EP | 0 289 204 A2 | 11/1988 |
| EP | 0311091 | 4/1989 |
| EP | 0336662 | 10/1989 |
| EP | 0393747 | 10/1990 |
| EP | 0 576 294 A2 | 12/1993 |
| EP | 0825858 | 3/1998 |
| EP | 0970623 | 1/2000 |
| EP | 1 310 249 A1 | 5/2003 |
| EP | 1 367 066 | 12/2003 |
| EP | 1755565 | 2/2007 |
| GB | 836082 | 6/1950 |
| GB | 2090529 | 7/1982 |
| GB | 2 223 943 A | 4/1990 |
| IL | 82459 | 7/1994 |
| JP | 55/015444 | 2/1980 |
| JP | 55/154533 | 12/1980 |
| JP | 58-62120 | 4/1983 |
| JP | 59-31711 | 2/1984 |
| JP | 59-039834 | 3/1984 |
| JP | 62-195324 | 8/1987 |
| JP | 62201823 | 9/1987 |
| JP | 64-013021 | 1/1989 |

(Continued)

OTHER PUBLICATIONS

Andrea Belluzzi, M.D., et al., "Effect of an Enteric-Coated Fish-Oil Preparation on Relapses in Crohn's Disease", The New England Journal of Medicine, vol. 334, No. 24, Jun. 13, 1996, pp. 1557-1560, XP-002111589.
Lee Goldman, M.D., et al., Cecil Textbook of Medicine, Chapter 198, pp. 1060-1074 W.B. Saunders Company (2000).
Communication of a notice of Opposition for European Patent No. EP1755565, dated Dec. 6, 2010.
Opposition to European Patent No. EP1755565 by Catalent Pharma Solutions. Inc., dated Nov. 17, 2010.
Affidavit of Dennis Rowe, with Exhibits 1-9, from Opposition to European Patent No. EP1755565 by Catelent Pharma Solutions, Inc.
Opposition to European Patent No. EP 1755565 by SPA Societa' Prodotti Antibiotici S.P.A. dated Nov. 17, 2010.

(Continued)

*Primary Examiner* — Raymond Henley, III
(74) *Attorney, Agent, or Firm* — Oblon, Spivak, McClelland, Maier & Neustadt, L.L.P.

(57) ABSTRACT

A pharmaceutical formulation comprising at least one omega-3 polyunsaturated fatty acid in free acid form or a pharmacologically acceptable derivative thereof is contained in a soft gelatin capsule characterized in that the capsule comprises gelatin extracted by an extraction process comprising acid pre-treatment of a collagen source. One advantage of the present invention over a soft gelatin capsule containing the same formulation but comprising gelatin extracted by an extraction process comprising alkali pre-treatment of the collagen source is that the present invention does not harden significantly over time and thus has a longer shelf life.

20 Claims, No Drawings

FOREIGN PATENT DOCUMENTS

| | | |
|---|---|---|
| JP | 64-038019 | 2/1989 |
| JP | 64/083021 | 3/1989 |
| JP | 02/103289 | 4/1990 |
| JP | 03/002119 | 1/1991 |
| JP | 04/066528 | 3/1992 |
| JP | 6-135851 | 5/1994 |
| JP | 07/041421 | 2/1995 |
| JP | 11-106333 | 4/1999 |
| JP | 2001335481 | 12/2001 |
| JP | 2003-510348 | 3/2003 |
| JP | 2003-146874 | 5/2003 |
| JP | 2003-516730 | 5/2003 |
| WO | WO 90/04391 | 5/1990 |
| WO | WO 92/14452 | 9/1992 |
| WO | WO 93/21912 | 11/1993 |
| WO | WO 94/28911 | 12/1994 |
| WO | WO 01/24780 A2 | 4/2001 |
| WO | WO 01/34646 A2 | 5/2001 |
| WO | 03/068216 | 8/2003 |
| WO | WO 03/080032 A2 | 10/2003 |
| WO | WO 03/086104 A1 | 10/2003 |
| WO | 03/103582 | 12/2003 |
| WO | WO 2004/091317 A1 | 10/2004 |
| WO | WO 2005/123060 A1 | 12/2005 |

OTHER PUBLICATIONS

Opposition to European Patent No. EP 1755565 by Pronova BioPharma Norge AS, dated Nov. 17, 2010.
Document D1 from Opposition to European Patent No. EP 1755565 by Pronova BioPharma Norge AS, Omega-3-acid Ethyl Esters (European Pharmacopoeia 2001).
Document D2 from Opposition to European Patent No. EP 1755565 by Pronova BioPharma Norge AS, Omega-3-acid Triglycerides (European Pharmacopoeia 2001).
Document D3 from Opposition to European Patent No. EP 1755565 by Pronova BioPharma Norge AS, "Product/Package Information for 'Seacor.'"
Document D4 from Opposition to European Patent No. EP 1755565 by Pronova BioPharma Norge AS, "Quality Report of Batch 05502 KL."
Document D5 from Opposition to European Patent No. EP 1755565 by Pronova BioPharma Norge AS, "Information Gelatin".
Document D10 from Opposition to European Patent No. EP1755565 by Pronova BioPharma Norge AS, "G. Reich, Formulation and Physical Properties of Soft Capsules from 'Pharmaceutical Capsules' by Podreck and Brain Jones, Chapter 11, Pharmaceutical Press 2004."
International Search Report issued Nov. 3, 2005 in PCT/GB2005/000415.
International Preliminary Report on Patentability issued Jun. 2, 2006 in PCT/GB2005/000415.
English translation of an Office Action issued Jan. 6, 2011 in Japanese Patent Application No. 2006-552677.
Japanese Office Action issued Nov. 18, 2011 in patent application No. 2006-552677 with English Translation.
Ansel, H., et al., "Ansel Drug Delivery Systems," Pharmaceutical Dosage Forms and Drug Delivery Systems, Sixth Edition, William & Wilkins, Media, Pennsylvania, p. 210 (1995).
Belluzzi, A., et al., "Effects of New Fish Oil Derivative on Fatty Acid Phospholipid-Membrane Pattern in a Group of Crohn's Disease Patients," Digestive Diseases and Sciences, vol. 39, No. 12, pp. 2589-2594 (1994).
Ghebre-Sellassie, I., et al., "Application of Eudragit E 30 D in Controlled-Release Coatings," Chapter 5—Aqueous Polymeric Coatings for Pharmaceutical Dosage Forms, J. McGinity, ed., Marcel Dekker, Inc., New York, NY, pp. 247-266 (1989).
Summons and Preliminary Opinion, EPO Opposition Division, EP 1 755 565 dated May 3, 2012.
Roger T Jones, "Gelatin: manufacture and physico-chemical properties", Pharmaceutical Capsules, Second edition, Edited by Fridrun Podczeck, 2004, pp. 23-60.
A. Belluzzi, "Polyunsaturated fatty acids (n-3 PUFAs) and inflammatory bowel disease (IBD): pathogenesis and treatment", European Review for Medical and Pharmacological Sciences, 2004; 8: pp. 225-229.
A. Belluzzi, "n-3 Fatty acids for the treatment of inflammatory bowel diseases", Proceedings of the Nutrition Society (2002), 61, pp. 391-395.
A. B. Hawthorne, et al., "Treatment of ulcerative colitis with fish oil supplementation: a prospective 12 month randomised controlled trial", GUT, 1992, 33, pp. 922-928.
A. Belluzzi, et al., "Polyunsaturated fatty acid pattern and fish oil treatment in inflammatory bowel disease", GUT, 1993, 34, pp. 1289-1290.
A. Belluzzi, et al., "Polyunsaturated fatty acids and inflammatory bowel disease[1,2]", Am J Clin Nutr 2000; 71(suppl): pp. 339S-342S.
"Purepa", Drugs R&D Mar. 1999; 1(3): pp. 268-269.
Brian G. Feagan, et al., "Omega-3 Free Fatty Acids for the Maintenance of Remission in Crohn Disease, The Epic Randomized Controlled Trials", JAMA, Apr. 9, 2008—vol. 299, No. 14, pp. 1690-1697.
"Handbook of Pharmaceutical Excipients", Second Edition, Edited by Ainley Wade and Paul J. Weller, 1994, pp. 362-366.
"Sustained-release coatings with EUDRAGIT NE 30 D from acqueous dispersions" Rohm, 2 pp . . . .
A. Belluzzi et al., "New Fish Oil Derivatives for Preventing Clinical Relapes in Crohn's Disease: A Double Blind Placebo Controlled Randomized Trial", Presented at the DDW, San Diego 1995, p. 799.
Martindale ("The complete drug reference"; $33^{rd}$ Edition; 2002; pp. 949.2 to 950.2 and 1956.3); 5 pages.
Extract for Macepa, from Monthly Index of Medical Specialties (MIMS) database on Oct. 31, 2011, 1 page.
SPC Omacor, eMC Medicine Guides, 5 pages, Summary of Product Characteristics last updated on ENC on Mar. 13, 2008.
Australian Public Assessment Report for Omega-3-acid ethyl esters 90, Oct. 2010, 2 pages.
Lovaza FDA label, Nov. 10, 2004, OMACOR, 9 pages.
FDA Product Label for OMACOR from Nov. 10, 2004.
Extract from Opponent 3 website on Oct. 27, 2011 entitled "Global distribution through strong partners" Pronova 2007 (http://www.pronova.com/Home/Product/Distribution_and partners/).
Rousselot leaflet 160 LP8, 2 pages, Nov. 24, 2010.
Extract for Pharmaton Matruelle from MIMS, 2 pages.
Extract for Pharmaton Matruelle from Catalog.md website (www.catalog.md).
Pamphlet from Microtek Laboratories, Inc. entitled "Microencapsulation", 5 pages.
Extracts for "Solf Elastic Capsules" and "Microencapsulation" from Remington: The Science and Practice of Pharmacy (2000), pp. 889 to 891.
Martindale, The complete drug reference, Martindale $33^{rd}$ edition, 2002, gelatin, 3 pages.
Letter of Dec. 19, 2011 submitted in EP opposition proceeding of EP 1755565B.
Letter of Jan. 26, 2012 submitted in EP opposition proceeding of EP 1755565B.
Letter of Sep. 13, 2012 by Weickmann, submitted in European opposition of corresponding EP 1755565.
Letter of Sep. 13, 2012 by Beck Greener, submitted in European opposition of corresponding EP 1755565.
Declaration of Olav Thorstad, dated Sep. 12, 2012.
Declaration of Harald Breivik, dated Sep. 4, 2012.
M.C. Lévy et al., "Microencapsulation par réticulation interfaciale de gélatine", S.T.P. Pharma 3 (8) 1987, pp. 644-651 w/English translation.
Excerpt of IF97 (Parte 1—Medicinali), pp. 835 and two front pages of the book Medicinali, 57th ed., 1, 1997, L'Informatore Farmaceutico w/English translation.
Excerpt of IF98 (Parte 1—Medicinali), pp. 837 and two front pages of the book Medicinali, 58th ed., 1, 1998, L'Informatore Farmaceutico w/English translation.
Declaration of Abdul Waseh Basit, dated Jul. 20, 2012.
Declaration of Thomas Buser, dated Sep. 10, 2012.
Report from Dr. Henry Wu of K&L Consulting Services Limited, Omthera Clinical Development, Epanova Drug Product Stability Analysis Report, dated Sep. 10, 2012.

Affidavit of Dennis Rowe, with Exhibits 1-9, from Opposition to European Patent No. EP1755565 by Catalent Pharma Solutions, Inc., Nov. 17, 2010.

Document D1 from Opposition to European Patent No. EP 1755565 by Pronova BioPharma Norge AS, Omega-3-acid Ethyl Esters (European Pharmacopoeia Sep. 20, 2001).

Document D2 from Opposition to European Patent No. EP 1755565 by Pronova BioPharma Norge AS, Omega-3-acid Triglycerides (European Pharmacopoeia Sep. 20, 2001).

Document D3 from Opposition to European Patent No. EP 1755565 by Pronova BioPharma Norge AS, "Product/Package Information for 'Seacor.'", submitted to EPO on Nov. 17, 2010.

Document D4 from Opposition to European Patent No. EP 1755565 by Pronova BioPharma Norge AS, "Quality Report of Batch 05502 KL." Nov. 19, 1998.

Document D5 from Opposition to European Patent No. EP 1755565 by Pronova BioPharma Norge AS, "Information Gelatin", submitted to EPO Nov. 17, 2010.

Letter of Oct. 26, 2012 by Weickmann, submitted in European opposition of corresponding EP 1755565.

Letter of Oct. 26, 2012 by Beck Greener, submitted in European opposition of corresponding EP 1755565.

Extract from European Pharmacopoeia—Supplement 2001 regarding "Capsules", pp. 1636-1638.

Information Sheet for "Pharmaceutical Gelatin", Rousselot 150 LP8 (Jan. 6, 2004), 1 page.

Letter of Sep. 26, 2012 by Weickmann, submitted in European opposition of corresponding EP 1755565.

Excerpt of IF97 (Part I) and two front pages of the book Medicinali 57$^{th}$ edition, L'Informatore Farmaceutico 1997.

Excerpt of IF98 and two front pages of the book Medicinali 58th edition, L'Informatore Farmaceutico 1998.

* cited by examiner

TYPE A GELATIN CAPSULE CONTAINING PUFA IN FREE ACID FORM

This application is a continuation of and claims priority benefit from U.S. patent application Ser. No. 10/587,201, filed May 15, 2007, now, U.S. Pat. No. 7,960,370, which is a U.S. National Stage Entry of International Patent Application No. PCT/GB2005/000415, filed Feb. 7, 2005, which in turn claims priority benefit from Great Britain Patent Application No. 0403247.0, filed Feb. 13, 2004, each of which is incorporated herein by reference in its entirety.

The present invention relates to a soft gelatin capsule and, in particular, to a soft gelatin capsule containing a pharmaceutical formulation comprising at least one omega-3 polyunsaturated fatty acid in free acid form or a pharmacologically acceptable derivative thereof.

Gelatin is a heterogeneous mixture of water-soluble proteins of high molecular weight extracted from a number of sources of collagen such bovine bones and hide, pig skin or fish skin. Broadly speaking, there are two types of gelatin, Type A gelatin and Type B gelatin, depending on the method of extraction.

According to "Gelatin Processing" (US National Organic Standards Board Technical Advisory Panel Review; 1 Mar. 2002), Type A gelatin is extracted following an acid pre-treatment process and porcine gelatin is usually extracted in this way. Pigskins are dehaired and degreased and the resultant skin is passed through a chopper or macerator to cut the skin into uniform sizes. The skin is then soaked at a pH of 1 to 4 with a food-grade mineral acid such as hydrochloric acid, phosphoric acid or sulphuric acid for 8 to 30 hours. The acid-treated pigskin is then washed with water to remove impurities and extracted with hot water. The extract is filtered through an anion-cation exchange column to reduce ash or mineral levels. The gelatin extract is vacuum concentrated or ultra filtered to a concentration between 15 to 35%, filtered, pH adjusted to between 3.5 and 6, and evaporated to 50% solids. The residue is chilled, extruded, dried and milled to the required particle size and then packaged. It is also known to pre-treat bovine ossein (de-mineralised bone) with acid prior to extraction of the gelatin although bovine ossein is more commonly pre-treated with alkali.

Type B gelatin is extracted following an alkali pre-treatment process and bovine gelatin is usually extracted in this way (ibid). Bones are crushed, cooked, centrifuged and dried. The extracted bone is degreased prior to gelatin extraction and de-mineralised with 4 to 6% hydrochloric acid for a period of 5 to 7 days. The ossein is washed repeatedly with water to remove impurities and then treated with 1 to 4% lime (calcium hydroxide) slurry to adjust the pH to about 12 for periods of 35 to 70 days with agitation and weekly lime changes to remove non-collagen components. The ossein is then washed and mineral acid is added to neutralise excess lime and adjust the pH to 3. The final pH after all wash operations is between 5 and 7. De-mineralised hot water is then used to extract the gelatin. The liquid gelatin solution may be filtered through a cellulose/diatomaceous earth plate and frame filter and deionised using an anionic-cationic resin bed. The resin solution is evaporated to a concentration between 15 to 45%. The concentrated gelatin is filtered, pH adjusted to between 5 and 7, sterilised, cooled and air-dried. It is then milled to the required size and packaged. The alkaline process may take up to 20 weeks.

Gelatin is used, for example, to encapsulate various foods and nutritional supplements but especially medicines for oral administration to treat a number of conditions. Plasticizers such as glycerine may be added to gelatin to produce soft gelatin capsules. Formaldehyde and other aldehydes may be used to harden gelatin capsules and enable them to pass from the stomach to the intestines. The vast majority of soft gelatin capsules are manufactured from Type B, e.g. bovine, gelatin.

Omega-3 polyunsaturated fatty acids such as 5, 8, 11, 14, 17-eicosapentaenoic acid (or "EPA") or 4, 7, 10, 13, 16, 19-docosahexaenoic acid (or "DHA") are well known to be useful in the treatment of inflammatory bowel disease (or "IBD") (see, for example, EP-A-0244832, EP-A-0289204, EP-A-0311091 and WO-A-93/21912, the disclosures of which are incorporated herein by reference). WO-A-96/36329 (Buser et al; published on 21 Nov. 1996) discloses a treatment of IBD involving oral administration of hard gelatin capsules containing a formulation that comprises a mixture of EPA and DHA. Each capsule is film coated with Eudragit™ NE 30-D which is an enteric material comprising poly(ethylacrylate-methylmethacrylate) having an average molecular weight of about 800,000. The capsules pass through the stomach and then disintegrate and release the contents in the small intestine. Results indicate that clinical relapses in Crohn's disease may be prevented by the oral administration of such coated capsules.

It is disclosed in U.S. Pat. No. 2,870,062 (Scherer et al; published on 20 Jan. 1959) that "standard gelatin capsules" disintegrate in contact with deliquescent or hygroscopic chemicals, such as liquid non-ionic detergents, salts of strong acids and bases, choline chloride and chloral hydrate, encapsulated within. U.S. Pat. No. 2,870,062 discloses the use of capsules made from specially selected low viscosity, high Bloom strength gelatin prepared from acid treated bone precursor. Such capsules do not appear to disintegrate when left in contact with deliquescent or hygroscopic chemicals.

EP-A-0100052 (Yu; published on 8 Feb. 1984) discloses soft gelatin capsules containing PGE-type prostaglandin fatty acid compositions. Comparative studies appear to indicate that soft gelatin capsules made from Type B gelatin accelerate degradation of the prostaglandin composition whereas soft gelatin capsules made from Type A gelatin retain the stabilising effect of the solvent in which the prostaglandin fatty acids are dissolved.

U.S. Pat. No. 6,234,464 (Krumbholz et al; published on 22 May 2001) discloses microencapsulated unsaturated fatty acids or fatty acid compounds or mixtures thereof. The wall of the microcapsules comprises two layers. The inner layer is composed of bone gelatin (gelatin A or gelatin B), casein or an alginate or by a derivative or salt thereof and the outer layer is composed of gelatin B, gum arabic, pectin or chitosan or a derivative or salt thereof. The unsaturated fatty acid may be an omega-3 fatty acid or and ethyl ester or glyceride thereof. U.S. Pat. No. 6,234,464 exemplifies microencapsulated 95% EPA ethyl ester in which the wall of each microcapsule comprises an inner/outer layer combination of gelatin A/gum arabic, gelatin A/pectin or gelatin A/gelatin B.

The inventors have discovered that, under certain conditions, soft gelatin capsules made from Type B gelatin and containing a pharmaceutical formulation comprising omega-3 polyunsaturated fatty acids can harden over time, even in the presence of plasticizers in the gelatin and have concluded that the hardening is due to chemical interaction between the omega-3 polyunsaturated fatty acid formulation and the gelatin itself. Such a hardening effect can reduce the shelf life of the capsules as, when the hardened capsules are administered orally, they pass not only through the stomach but also though the small intestine and may even pass through a substantial part of the large intestine before the capsule disintegrates and the pharmaceutical formulation is released. If the capsules are being administered as a treatment of IBD then release of the omega-3 polyunsaturated fatty acid formulation beyond the small intestine will not be effective in this treatment. It is, therefore, an object of preferred embodiments of the present invention to provide a soft gelatin capsule containing an omega-3 polyunsaturated fatty acid formulation that displays a reduced hardening rate and thereby has an increased shelf life when compared to existing soft gelatin capsules containing omega-3 polyunsaturated fatty acids.

Disintegration of a soft gelatin capsule in vivo occurs not only though dissolution in an aqueous medium but also through the action of proteases on the gelatin. However, the chemical interaction between the omega-3 polyunsaturated fatty acid and the gelatin is uncontrolled and may continue throughout the shelf life of the product. In addition, a coating on the capsule will usually hinder the action of the proteases thereby reducing their effectiveness.

According to a first aspect of the present invention, there is provided a soft gelatin capsule containing a pharmaceutical formulation comprising at least one omega-3 polyunsaturated fatty acid ("PUFA") in free acid form or a pharmacologically acceptable derivative thereof characterised in that the capsule comprises gelatin extracted by an extraction process comprising acid pre-treatment of a collagen source.

One advantage of this type of soft gelatin capsule is that the rate of hardening is significantly less than that for existing soft gelatin capsules (containing an omega-3 polyunsaturated fatty acid formulation) comprising gelatin extracted by an extraction process comprising alkali pre-treatment of a collagen source. The reduced rate of hardening translates into an increased shelf life for the capsules. A further advantage is that it is possible to move away from gelatin made from bovine bones and hides. In recent years, there has been some concern regarding the possible transmission of spongiform encephalopathies such as bovine spongiform encephalopathy (or "BSE") to humans. Type A gelatin, or gelatin extracted by an extraction process comprising acid pre-treatment of a collagen source, is usually made from pig skin and, thus, the use of such gelatin for the manufacture of soft gelatin capsules avoids any risk of contracting BSE from bovine Type B gelatin.

The decrease in hardening rate is surprising and unexpected as porcine gelatin (usually Type A gelatin) and bovine gelatin (usually Type B gelatin) have basically the same chemical structure in that the amino acid residues in both types of gelatin are essentially identical. Therefore, the skilled person would not expect the two types of gelatin to interact differently with the same omega-3 polyunsaturated fatty acid.

The omega-3 polyunsaturated fatty acid is preferably present in the form of the free acid. However, pharmacologically acceptable derivatives may also be used. Examples of suitable derivatives include triglycerides, esters (such as ethyl ester), amides, complexes (e.g. with bile salts, cholesterol or chitosan) and salts (such as sodium or potassium salts). In preferred embodiments, the formulation consists essentially of at least one omega-3 polyunsaturated fatty acid in free acid form or a pharmacologically acceptable derivative thereof but usually further comprises additives such as antioxidants, e.g. α-tocopherol.

Preferably, the formulation comprises 5, 8, 11, 14, 17-eicospentenoic acid (or "EPA"). EPA may present in an amount of at least about 50 wt % and preferably between from about 50 wt % to about 60 wt % of the formulation although it may also be desirable to have EPA present in an amount of at least about 90 wt % of the formulation for certain applications and/or to minimise the number of capsules needed to be taken to provide a therapeutically active dose.

The formulation may comprise 4, 7, 10, 13, 16, 19-docosahexaenoic acid (or "DHA"). DHA may be present in an amount of between from about 20 wt % to about 30 wt % of the formulation.

The soft gelatin capsule preferably comprises between from about 100 mg to about 2000 mg of said formulation. At present, two embodiments of the capsule are preferred, the first embodiment comprising about 500 mg of said formulation and intended for use, for example, with children and the second embodiment comprising about 1000 mg intended for adult use.

The gelatin used is preferably at least one selected from the group consisting of porcine gelatin, bovine gelatin and fish gelatin, provided that the gelatin has been extracted by an extraction process comprising acid pre-treatment of the relevant collagen source. Mixtures of these gelatins may also be used.

The wall of each of the soft gelatin capsules of the present invention usually consists of only one layer.

Soft gelatin capsules of the present invention may be used in the treatment or prophylaxis of chronic inflammatory conditions such as inflammatory bowel disease, Crohn's disease, ulcerative colitis, rheumatoid arthritis, psoriasis or Behçet's syndrome; hyperlipidaemia or hypertriglyceridaemia; asthma; bipolar disorder; and neoplastic disease such as prostate cancer or bowel cancer. In certain preferred embodiments, the soft gelatin capsule will be used to treat or prevent IBD or Crohn's disease. In addition, the capsules may be used to prevent post-operative recurrence of Crohn's disease.

If administered parenterally, immunosuppressants (e.g. methotrexate or cyclosporin) or antineoplastic agents (e.g. methotrexate) often have adverse systemic side effects. GB0413729.5 (filed on 18 Jun. 2004) describes the use of PUFA or a pharmacologically acceptable salt or derivative thereof in combination with at least one of an immunosuppressant and an antineoplastic agent, said agent(s) having at least one amino acid residue, or a pharmacologically acceptable salt or derivative thereof in the manufacture of a medicament for the treatment of intestinal conditions. GB0413730.3 (filed on 18 Jun. 2004) describes the use of PUFA or a pharmacologically acceptable salt or derivative thereof in combination with at least one of an immunosuppressant and an antineoplastic agent or a pharmacologically acceptable salt or derivative thereof in the manufacture of a medicament for the topical treatment of intestinal conditions. The effect of the PUFA in the uses disclosed in GB0413730.3 and GB0413729.5 is to increase the oral bioavailability of the immunosuppressant and antineoplastic agent, thereby allowing less agent(s) to be administered and reducing the side effects. The disclosures of GB0413729.5 and GB0413730.3 are incorporated herein by reference.

The soft gelatin capsules of the present invention may be used to provide the PUFA to achieve this sparing effect for immunosuppressants such as methotrexate, cyclosporin, dactinomycin, 6-mercaptopurine, cyclophosphamide, mycophenolate, daclizumab, muromonab, predisolone, sirolimus, dexamethasone, rapamycin, FK506, mizoribine, azathioprine, tacrolimus and infliximab and for antineoplastic agents such as methotrexate, dactinomycin, fluorouracil, bleomycin, etoposide, taxol, vincristine, doxorubicin, cisplatin, daunorubicin and VP-16.

EP-A-1054678 discloses the use of PUFAs as steroid sparing agents. The soft gelatin capsule of the present invention could be used to provide the PUFA to spare steroids such as budesonide or prednisolone. The disclosure of EP-A-1054678 is incorporated herein by reference.

The capsule preferably delays release of the formulation until after passage through the stomach. Release preferably occurs after passage beyond the pancreatic duct in the duodenum and, more preferably, in the ileum. Preferably, release should not occur after the mid-jejunum. Release is typically delayed for at least 30 minutes after oral administration and preferably for between 30 to 60 minutes at pH 5.5. Release of the formulation begins after the integrity of the capsule wall is compromised, i.e. after dissolution or perforation of the gelatin wall. If release occurs due to the gelatin capsule becoming porous, then release may also be sustained which may be advantageous, especially in the treatment of IBD or Crohn's disease.

Release may be delayed by coating the capsule with at least one enteric material that is resistant to dissolution in a time dependent and/or pH dependent manner. Alternatively or additionally, at least one such enteric material is integrated within the gelatin of the capsule. Preferably, a time but not pH dependent release coating material is used. A preferred enteric material is a neutral polyacrylate such as poly(ethylacrylate-methylmethacrylate), especially Eudragit NE 30-D (Röhm Pharma GmbH) which has an average molecular weight of about 800,000 and is an example of a time but not pH dependent release coating material.

According to a second aspect of the present invention, there is provided use of gelatin extracted by an extraction process comprising acid pre-treatment of a collagen source in the manufacture of a medicament comprising at least one soft gelatin capsule as defined in the first aspect for the oral treatment or prophylaxis of a condition selected from chronic inflammatory conditions, hyperlipidaemia, hypertriglyceridaemia, asthma, bipolar disorder and neoplastic disease. The medicament has particular application in the treatment or prophylaxis of inflammatory bowel disease ("IBD") or Crohn's disease. The medicament may comprise at least one soft gelatin capsule having any of the preferred features discussed above in any appropriate combination.

According to a third aspect of the present invention, there is provided a process for the manufacture of a soft gelatin capsule containing a pharmaceutical formulation comprising at least one omega-3 polyunsaturated fatty acid in free acid form or a pharmacologically acceptable derivative thereof, said process comprising encapsulating said pharmaceutical formulation in gelatin extracted by an extraction process comprising acid pre-treatment of a collagen source.

According to a fourth aspect of the present invention, there is provided use of gelatin extracted by an extraction process comprising acid pre-treatment of a collagen source in a soft gelatin capsule containing a pharmaceutical formulation comprising at least one omega-3 polyunsaturated fatty acid in free acid form or a pharmacologically acceptable derivative thereof to improve resistance of the soft gelatin capsule to chemical interaction with the formulation. Preferably, said resistance is greater than that of a soft gelatin capsule containing a pharmaceutical formulation comprising at least one omega-3 polyunsaturated fatty acid in free acid form or a pharmacologically acceptable derivative thereof in which the gelatin consists essentially of gelatin extracted by an extraction process comprising alkali pre-treatment of a collagen source.

According to a fifth aspect of the present invention, there is provided use of gelatin extracted by an extraction process comprising acid pre-treatment of a collagen source in a soft gelatin capsule containing a pharmaceutical formulation comprising at least one omega-3 polyunsaturated fatty acid in free acid form or a pharmacologically acceptable derivative thereof to improve shelf life of the soft gelatin capsule. Preferably, said shelf life is greater than that for a soft gelatin capsule containing a pharmaceutical formulation comprising at least one omega-3 polyunsaturated fatty acid in free acid form or a pharmacologically acceptable derivative thereof in which the gelatin consists essentially of gelatin extracted by an extraction process comprising alkali pre-treatment of a collagen source.

The soft gelatin capsule may be used in the treatment or prophylaxis of IBD and, in particular, Crohn's disease. In such treatment or the other treatments listed above, the daily dosage of the formulation would be set by the doctor in charge of the patient and would depend on a number of factors such as age. Usually, between from about 1 g to about 8 g of the formulation is administered to the patient per day, particularly in the treatment of IBD or Crohn's disease. Administration may be in the form of a plurality of soft gelatin capsules according to the first aspect of the present invention. The total number of capsules administered daily will depend on the amount of the formulation in each capsule. Thus, for example, a daily dose of 4 g of formulation might be administered in the form of either 8 500 mg capsules or 4 1000 mg capsules and a daily dose of 8 g of formulation might be administered in the form of 8 1000 mg capsules.

According to a sixth aspect of the present invention, there is provided a method of treatment or prophylaxis of a condition selected from chronic inflammatory conditions, hyperlipidaemia, hypertriglyceridaemia, asthma, bipolar disorder and neoplastic disease comprising administering a therapeutically effective amount of a pharmaceutical formulation comprising at least one omega-3 polyunsaturated fatty acid in free acid form or a pharmacologically acceptable salt thereof per day in the form of a plurality of soft gelatin capsules according to the first aspect of the present invention. Where the condition to be treated or prevented is IBD or Crohn's disease, the therapeutically effective amount is usually from about 1 g to about 8 g. The capsules may have any of the preferred features discussed above in any appropriate combination.

The following is a description, by way of example only, of a presently preferred embodiment of the present invention.

Type A gelatin capsules were formed and simultaneously filled with an omega-3 polyunsaturated fatty acid formulation in a known manner. Type A porcine gelatin powder was mixed with water and plasticizer and then heated to form a molten gelatin mass. Two thin ribbons of the molten gelatin were produced and passed between two die rolls which determined the shape of the capsules. The formulation was injected between the two gelatin ribbons just before the die rolls sealed the capsules together by application of heat and pressure. The resulting capsule was then dried to the required moisture content.

The stability of the Type A gelatin capsules produced in this manner was compared with that for the Type B gelatin capsules produced using the same process. Batches of both capsules were stored for different periods (3 months, 6 months, 9 months and 12 months) and at different temperatures (25° C., 30° C. and 40° C.) and then the disintegration times of the capsules in purified water at 37° C. according to Ph. Eur. were measured. The results are indicated in Table 1.

TABLE 1

| Capsule | Storage Temp (° C.) | 0 months | 3 months | 6 months | 9 months | 12 months |
|---|---|---|---|---|---|---|
| Type B gelatin (Bovine) | 25 | 7 min | 9 min | 9 min | 6 min | 10 min |
|  | 30 | 7 min | 9 min | 20 min | n.p. | Insoluble |
|  | 40 | 7 min | Insoluble | Insoluble | n.p. | n.p. |
| Type A gelatin (Porcine) | 25 | 6 min | 6 min | 7 min | 6 min | 7 min |
|  | 30 | 6 min | 7 min | 8 min | n.p. | 10 min |
|  | 40 | 6 min | 8 min | 10 min | n.p. | n.p. |

It should take no longer than 30 min for a soft gelatin capsule to disintegrate if it is to release its contents effectively. Therefore, if a capsule failed to disintegrate in 30 min, it was deemed "insoluble". The term "n.p." indicated that the test was "not performed".

The results indicate that, for the Type B (bovine) gelatin capsules stored at a given temperature, there is a general increase in disintegration time as the storage time increases. In addition, for the Type B (bovine) gelatin capsules stored for a given time, there is a general increase in disintegration time as the storage temperature increases. These results are consistent with the omega-3 polyunsaturated fatty acid interacting chemically with the Type B gelatin resulting in a hardening of the capsule wall.

In contrast, disintegration time is not substantially increased for the Type A (porcine) gelatin capsules as either the storage time or storage temperature increases. These results would appear to indicate that the degree of hardening is significantly less for Type A (porcine) gelatin capsules than for Type B (bovine) gelatin capsules. In particular, attention is drawn to the disintegration results for the Type B (bovine) gelatin capsules stored at 30° C. for 12 months and at 40° C. for 3 months and 6 months as these capsules have been classified as "insoluble" whereas the corresponding Type A (porcine) gelatin capsules took no more than 10 minutes to dissolve.

It will be appreciated that the invention is not restricted to the details described above with reference to the preferred embodiments but that numerous modifications and variations can be made without departing from the spirit or scope of the invention as defined by the following claims.

The invention claimed is:

1. A soft gelatin capsule, comprising:
   inside said capsule, a pharmaceutical composition comprising at least about 50 wt % of 5,8,11,14,17-eicosapentaenoic acid in free acid form, and
   wherein said capsule comprises sufficient porcine Type A gelatin such that the capsule disintegrates within a time period of not more than 30 min in purified water at 37° C. after storage for at least 3 months at 40° C.

2. The soft gelatin capsule of claim 1, wherein said capsule comprises sufficient porcine Type A gelatin such that the capsule disintegrates within a time period of not more than 30 min in purified water at 37° C. after storage for 6 months at 40° C.

3. The soft gelatin capsule of claim 1, wherein said capsule comprises sufficient porcine Type A gelatin such that the capsule disintegrates within a time period of not more than 30 min in purified water at 37° C. after storage for 12 months at 40° C.

4. A soft gelatin capsule, comprising:
   inside said capsule, a pharmaceutical composition comprising at least about 50 wt % 5,8,11,14,17-eicosapentaenoic acid in free acid form, and
   wherein the gelatin of said capsule consists essentially of porcine Type A gelatin.

5. The soft gelatin capsule of claim 1, wherein said pharmaceutical composition comprises from about 50 wt % to about 60 wt % of 5,8,11,14,17-eicosapentaenoic acid in free acid form.

6. The soft gelatin capsule of claim 1, wherein said pharmaceutical composition further comprises about 20 wt % to about 30 wt % of 4,7,10,13,16,19-docosahexaenoic acid in free acid form.

7. The soft gelatin capsule of claim 5, wherein said pharmaceutical composition further comprises about 20 wt % to about 30 wt % of 4,7,10,13,16,19-docosahexaenoic acid in free acid form.

8. The soft gelatin capsule of claim 1, which comprises, inside said capsule, from about 100 mg to about 2000 mg of said pharmaceutical composition.

9. The soft gelatin capsule of claim 8, which comprises, inside said capsule, about 500 mg of the pharmaceutical composition.

10. The soft gelatin capsule of claim 8, which comprises, inside said capsule, about 1000 mg of the pharmaceutical composition.

11. The soft gelatin capsule of claim 8, further comprising a neutral polyacrylate coating.

12. The soft gelatin capsule of claim 11, wherein the coating is poly(ethylacrylate-methylmethacrylate).

13. A method of treating hypertriglyceridemia, comprising:
   administering to a patient with hypertriglyceridemia an effective number of soft gelatin capsules,
   wherein each capsule comprises, inside said capsule,
   a pharmaceutical composition comprising at least about 50 wt % of 5,8,11,14,17-eicosapentaenoic acid in free acid form, and
   wherein each capsule comprises sufficient porcine Type A gelatin such that the capsule disintegrates within a time period of not more than 30 min in purified water at 37° C. after storage for at least 3 months at 40° C.

14. The method of claim 13, wherein said pharmaceutical composition comprises from about 50 wt % to about 60 wt % of 5,8,11,14,17-eicosapentaenoic acid in free acid form.

15. The method of claim 13, wherein said pharmaceutical composition further comprises about 20 wt % to about 30 wt % of 4,7,10,13,16,19-docosahexaenoic acid in free acid form.

16. The method of claim 14, wherein said pharmaceutical composition further comprises about 20 wt % to about 30 wt % of 4,7,10,13,16,19-docosahexaenoic acid in free acid form.

17. The method of claim 13, wherein the soft gelatin capsule further comprises a neutral polyacrylate coating.

18. The method of claim 17, wherein the coating is poly(ethylacrylate-methylmethacrylate).

19. The method of claim 13, wherein a plurality of soft gelatin capsules is administered daily.

20. The method of claim 19, wherein each soft gelatin capsule comprises from about 100 mg to about 2000 mg of the pharmaceutical composition.

* * * * *